US00PP26584P3

(12) United States Plant Patent
Montecucco

(10) Patent No.: US PP26,584 P3
(45) Date of Patent: Apr. 5, 2016

(54) RHUBARB PLANT NAMED 'LMR2013'

(50) Latin Name: *Rheum rhabarbarum (syn. R.×cultorum)*
Varietal Denomination: LMR2013

(71) Applicant: Montecucco Farms, LLC, Canby, OR (US)

(72) Inventor: Edward Virgil Montecucco, Canby, OR (US)

(73) Assignee: Montecucco Farms, LLC, Canby, OR (US)

( * ) Notice: Subject to any disclaimer, the term of this patent is extended or adjusted under 35 U.S.C. 154(b) by 237 days.

(21) Appl. No.: 13/998,915

(22) Filed: Dec. 20, 2013

(65) Prior Publication Data

US 2015/0181790 P1 Jun. 25, 2015

(51) Int. Cl.
*A01H 5/12* (2006.01)

(52) U.S. Cl.
USPC ..... Plt./262

(58) Field of Classification Search
USPC ..... Plt./258, 262
See application file for complete search history.

*Primary Examiner* — Susan McCormick Ewoldt
*Assistant Examiner* — Karen Redden
(74) *Attorney, Agent, or Firm* — Klarquist Sparkman, LLP

(57) ABSTRACT

A new and distinct cultivar of rhubarb, *Rheum rhabarbarum*, characterized by foliage that doesn't senesce until temperatures get low enough for a hard frost (usually around 25 degrees F.), bright red petioles with excellent flavor and sweetness and vigorous growth.

4 Drawing Sheets

Botanical classification: *Rheum rhabarbarum* (syn. *R.×cultorum*).

Variety denomination: 'LMR2013'.

BACKGROUND OF THE INVENTION

The present invention relates to a new and distinct cultivar of *Rheum rhabarbarum*, and known by the cultivar name of 'LMR2013'. The genus *Rheum* is a member of the family Polygonaceae.

The new cultivar was a seedling found by the inventor in a cultivated area of a rhubarb farm in Canby, Oreg. The parentage of the new cultivar is unknown. It is unique in that it does not senesce until after a hard frost, giving a much longer production time for the petioles. In Canby, Oreg. production can continue up to 3 months longer than other varieties in a low frost year.

The closest comparison cultivar is believed to be *Rheum rhabarbarum* 'Crimson Red', an unpatented plant. Compared to *Rheum rhabarbarum* 'Crimson Red', the new cultivar has a redder, rounder petiole, and greater winter hardiness.

SUMMARY OF THE INVENTION

This new cultivar is characterized by:

1) foliage with excellent winter hardiness, that doesn't senesce until temperatures get low enough for a hard frost (usually around 25 degrees F.),
2) bright red petioles with excellent flavor and sweetness,
3) large fleshy petioles which are tender with low stringiness,
4) heavy yielding, and
5) vigorous growth.

The new variety has been reproduced by asexual propagation (division) in Canby, Oreg. Each of the progeny exhibits identical characteristics to the original plant. Asexual propagation by division with lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
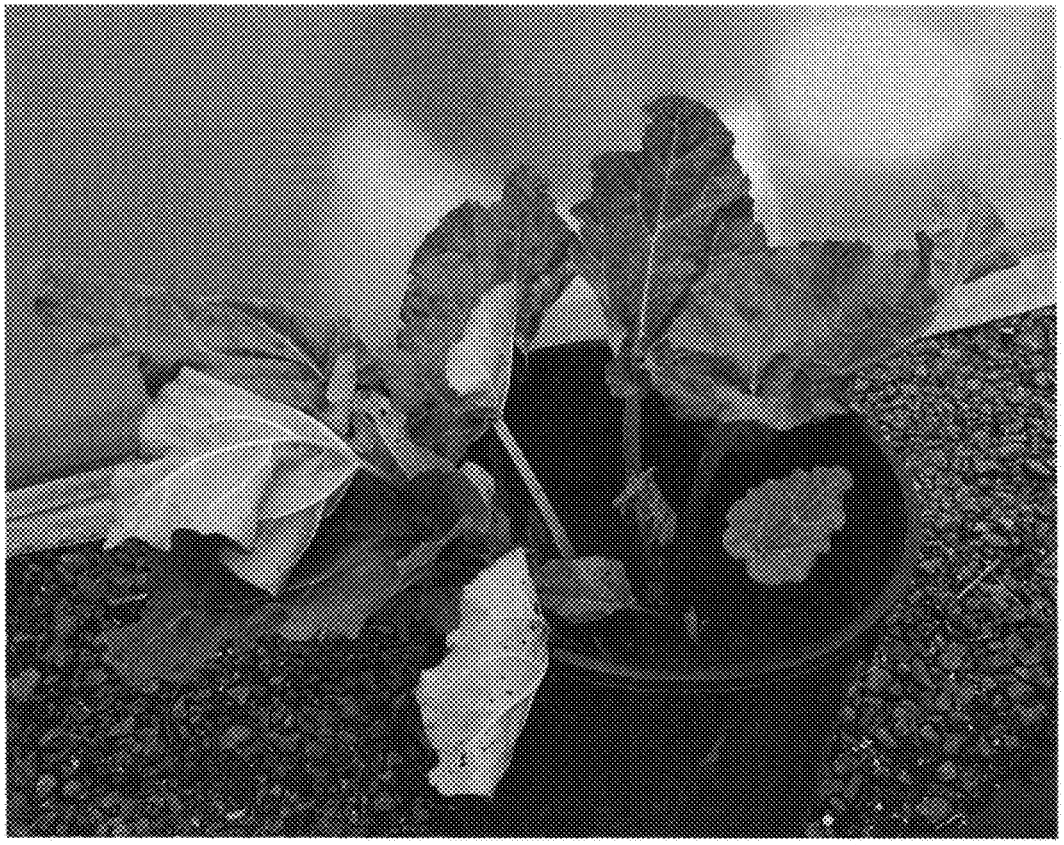
FIG. 1 shows one-year-old *Rheum* 'LMR2013' newly dug and in a 15 gallon container in May in Canby, Oreg.
Figure 2:
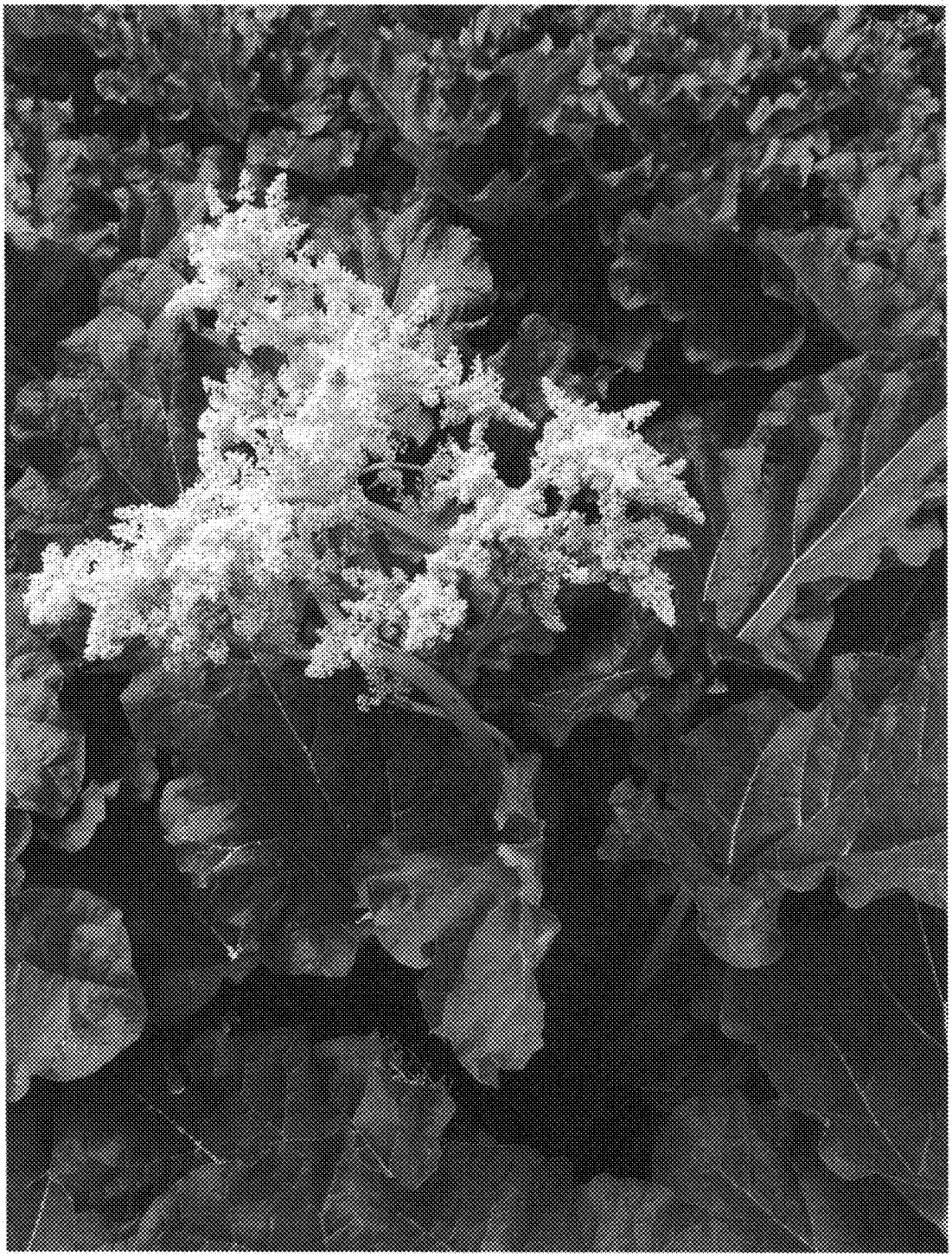
FIG. 2 shows a one year old plant in bloom growing in the field in late June in Canby, Oreg.
Figure 3:
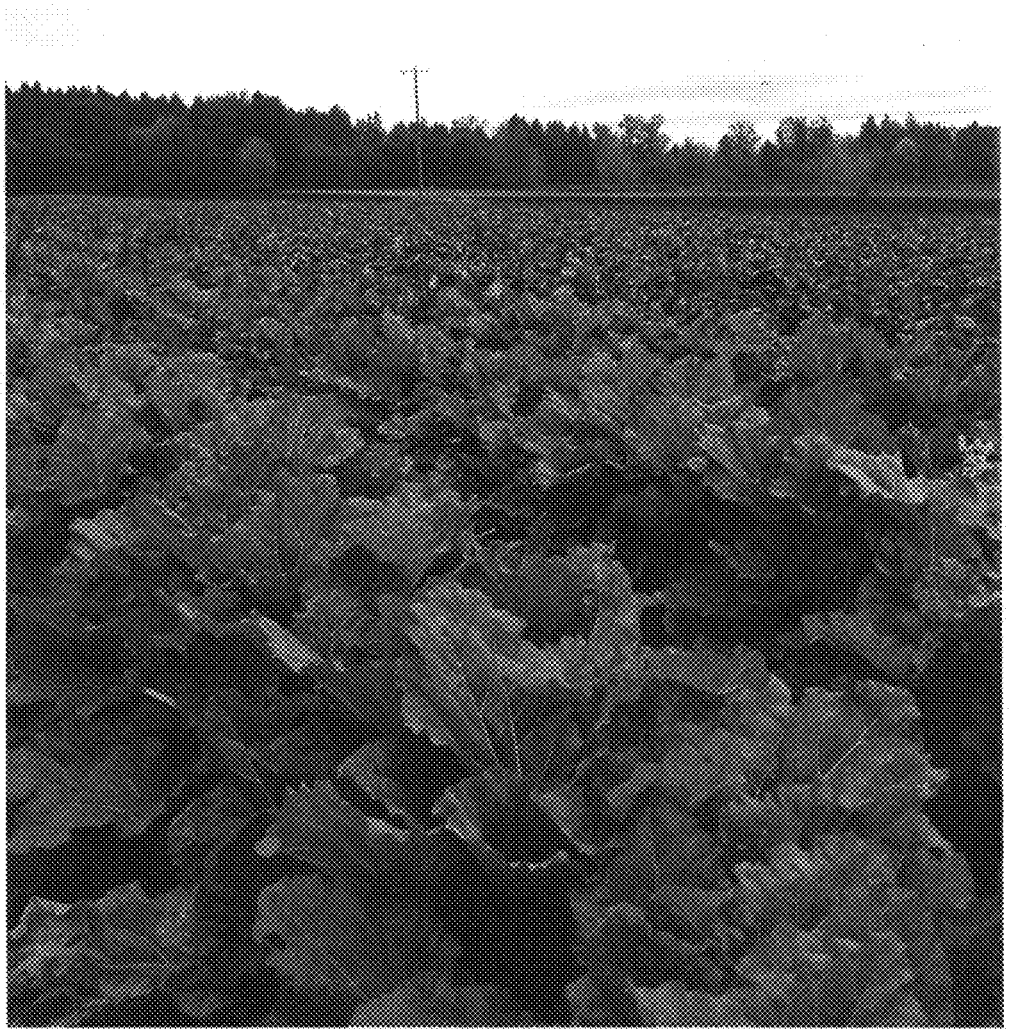
FIG. 3 shows the same plants in the field.
Figure 4:
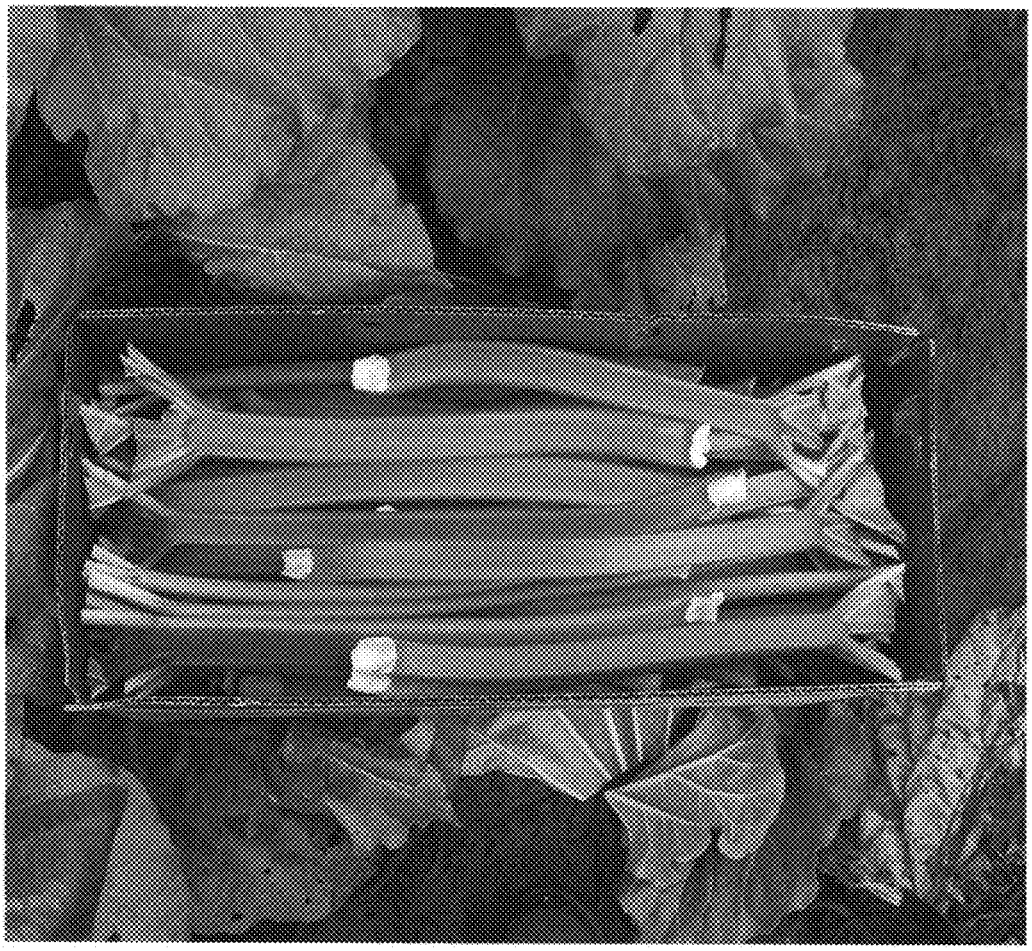
FIG. 4 shows the cut petioles in late October in the same field.

The following is a detailed description of the new cultivar based on observations of a typical one-year-old specimen dug from the field in Canby, Oreg. and put in a 15 gallon container. Canby is Zone 8 on the USDA Hardiness map. Temperatures range from a high of 95 degrees F. in August to an average of 32 degrees F. in January, but daily temperatures can be lower. Normal rainfall in Canby is 42.8 inches per year. The color descriptions are all based on *The Royal Horticultural Society Colour Chart,* 5th edition, published in 2007.

Plant:

*Type*.—Herbaceous rhizomatous perennial.

*Hardiness*.—Observed in USDA Zone 8.

*Time of emergence*.—With a hard frost, early spring in Canby, Oreg.; without a hard frost, still evergreen from the previous fall and producing new growth.

*Size*.—42 cm tall and 78 cm wide.
*Habit*.—Clumping, with 4 crowns.

Leaf:
*Type*.—Simple.
*Arrangement*.—Rosette.
*Shape*.—Ovate.
*Venation*.—Pinnate.
*Margins*.—Undulate.
*Apex*.—Obtuse.
*Base*.—Cordate with lobes curling up or overlapping at the base.
*Blade size*.—Typical — grows to 36 cm long and 28 cm wide.
*Surface*.—Glabrous above, sparsely pubescent on veins below.
*Petiole*.—Typical — 25 cm long and 2 cm wide and 1.4 cm thick near base, D-shaped in cross section, semi-erect in attitude, medium dorsal ribbing, Red Purple 59A when young and first mature, lightening to Red Purple 59A at base and speckled up the petiole over Yellow Green 146D; flesh color closest to Yellow green 145D.
*Leaf color*.—Topside Green 137A with veins Yellow Green 145C, bottom side Yellow Green 147C with veins Yellow Green 145D.

Inflorescence:
*Type*.—Large panicle on upright stem.
*Size of inflorescence*.—Typical — 29 cm wide and 72 cm long without peduncle, 149 cm tall with peduncle.
*Number of flowers*.—Typical would be about 5000.
*Peduncle*.—Typical — 48 mm wide and 77 cm long, hollow, 1 to 3 branched with petiolate leaf at branches (typical blade grows to 39 cm long and 26 cm wide, topside Green 137A with veins Yellow Green 145C, bottom side Yellow Green 147C with veins Yellow Green 145D), glabrous, Yellow Green 145C.
*Pedicel*.—3 to 5 mm long, glabrous, Yellow Green 145D.
*Bloom period*.—Late June to August in Canby, Oreg.

Flower bud:
*Size*.—Typical — 3 mm deep and 2.5 mm wide.
*Description*.—Ovoid.
*Color*.—White 155A.

Flower:
*Type*.—Perfect, actinomorphic.
*Shape*.—Campanulate.
*Size*.—About 3 mm deep and 3 mm wide.
*Perianth description*.—About 3 mm deep and 3 mm wide, 6 tepals, tip obtuse, margin entire, both sides glabrous and White 155A, 3 outer tepals obovate, about 1 mm long and 1 mm wide, cupped, 3 inner tepals obovate, about 1.5 mm long and 1.5 mm wide; stamen 9, about 2 mm long, White NN155A, anthers about 0.5 mm long, Yellow 16C, pollen 11C; ovary about 1 mm deep and 2 mm wide, White NN155A, triangular to box-shaped with 3-4 deflexed styles, styles less than about 1 mm long, head-like stigmas, about 1 mm wide.
*Fragrance*.—Unpleasant.
*Lastingness*.—Each panicle blooms for about 3 weeks on the plant.

Fruit: Three-to-four-sided achene with winged sides.

Seed: None observed.

Disease and pest resistance and tolerance: The new cultivar is typical to the genus. No known resistances to pests or diseases. No problems have been found in Canby, Oreg.

Market use: The new cultivar is primarily used for fresh sales. This is especially valuable in the late fall and winter months when other cultivars go dormant.

Shipping and storage: The new cultivar is stored and shipped in the same manner as other varieties of Rhubarb. The petiole is stored at 34 degrees F. and will store for approximately 10 days. This new cultivar will produce during the late fall through winter months when other cultivars are dormant.

Productivity: The estimated yield is approximately 700-20 lb cartons or 14,000 lbs/acre. The average weight of a petiole is approximately 3 oz.

I claim:

1. A new and distinct cultivar of *Rheum rhabarbarum* plant as herein shown and described.

* * * * *